(12) United States Patent
Sbaiz et al.

(10) Patent No.: US 11,896,490 B2
(45) Date of Patent: Feb. 13, 2024

(54) SCAPULAR ANCHOR FOR FIXING A GLENOID COMPONENT OF A SHOULDER JOINT PROSTHESIS TO A SCAPULA WITH COMPROMISED ANATOMY

(71) Applicant: LIMACORPORATE S.p.A., Villanova di San Daniele del Friuli (IT)

(72) Inventors: Fausto Sbaiz, Codroipo (IT); Michele Pressacco, Martignacco (IT)

(73) Assignee: LIMACORPORATE S.P.A., Villanova di San Daniele del Friuli (IT)

( * ) Notice: Subject to any disclaimer, the term of this patent is extended or adjusted under 35 U.S.C. 154(b) by 525 days.

(21) Appl. No.: 17/088,014

(22) Filed: Nov. 3, 2020

(65) Prior Publication Data
US 2021/0045888 A1 Feb. 18, 2021

Related U.S. Application Data

(62) Division of application No. 15/951,795, filed on Apr. 12, 2018, now Pat. No. 10,905,562.

(30) Foreign Application Priority Data

Apr. 13, 2017 (IT) .................. 102017000041420

(51) Int. Cl.
*A61F 2/40* (2006.01)
*A61F 2/30* (2006.01)

(52) U.S. Cl.
CPC ........ *A61F 2/4081* (2013.01); *A61F 2/30942* (2013.01); *A61F 2/40* (2013.01);
(Continued)

(58) Field of Classification Search
CPC .. A61F 2/40; A61F 2/4081; A61F 2002/4088; A61F 2002/4092; A61F 2002/4096
See application file for complete search history.

(56) References Cited

U.S. PATENT DOCUMENTS

| 4,919,669 A | 4/1990 | Lannelongue |
| 7,959,680 B2 | 6/2011 | Stone |

(Continued)

FOREIGN PATENT DOCUMENTS

EP 2 929 861 A1 10/2015

OTHER PUBLICATIONS

Sbaiz, U.S. Appl. No. 15/951,795, filed Apr. 12, 2018, Office Action dated Nov. 1, 2019.
(Continued)

*Primary Examiner* — Brian A Dukert
(74) *Attorney, Agent, or Firm* — Patterson & Sheridan LLP; Malgorzata A. Kulczycka

(57) ABSTRACT

Customizable scapular anchor (1) for fixing a glenoid component of a shoulder joint prosthesis to a patient's scapula with compromised anatomy, comprising a glenoid support (2), said glenoid support (2) being defined by a pin element (3) for fixing said glenoid component to said scapular anchor (1) and by a flange (4) integral with said pin element (3), said flange (4) having a distal surface (5) adapted to be placed at least partially in contact with a glenoid cavity of said scapula and a proximal surface (6) opposite said distal surface (5); wherein at least one customized portion (5, 7, 8) is specifically shaped with respect to the bone morphology of a single patient's scapula with compromised anatomy; the customized portion (5, 7, 8) comprises at least one coracoid support projection (7) arranged to abut at a coracoid process (52) of the scapula (50).

21 Claims, 11 Drawing Sheets

(52) U.S. Cl.
CPC ............... *A61F 2002/30604* (2013.01); *A61F 2002/30878* (2013.01); *A61F 2002/30948* (2013.01); *A61F 2002/4096* (2013.01)

(56) References Cited

U.S. PATENT DOCUMENTS

| | | |
|---|---|---|
| 8,532,806 B1 | 9/2013 | Masson |
| 2004/0133276 A1 | 7/2004 | Lang |
| 2006/0079963 A1 | 4/2006 | Hansen |
| 2007/0179624 A1 | 8/2007 | Stone et al. |
| 2014/0364953 A1 | 12/2014 | Tomlinson et al. |
| 2018/0296356 A1 | 10/2018 | Sbaiz |

OTHER PUBLICATIONS

Sbaiz, U.S. Appl. No. 15/951,795, filed Apr. 12, 2018, Notice of Allowance dated Jul. 31, 2020.
Sbaiz, U.S. Appl. No. 15/951,795, filed Apr. 12, 2018, Final Office Action dated Apr. 6, 2020.

SCAPULAR ANCHOR FOR FIXING A GLENOID COMPONENT OF A SHOULDER JOINT PROSTHESIS TO A SCAPULA WITH COMPROMISED ANATOMY

BENEFIT CLAIM

This application claims the benefit under 35 U.S.C. § 120 as a Divisional of application Ser. No. 15/951,795, filed Apr. 12, 2018, which claims the benefit of 102017000041420, filed Apr. 13, 2017, the entire contents of which are hereby incorporated by reference for all purposes as if fully set forth herein, under 35 U.S.C. § 119.

DESCRIPTION

Field of Application

The present invention relates to a scapular anchor for fixing a glenoid component of a shoulder joint prosthesis to a patient's scapula, in particular a scapula with a compromised anatomy.

Prior Art

As it is well known, the total shoulder prostheses provide a glenoid prosthetic component and a humeral component, which articulate with each other.

In the clinical practice two types of total shoulder prostheses are used.

A first type of prosthesis, defined anatomic and aimed at reproducing the natural anatomy of the glenohumeral joint, provides a humeral component with convex end that articulates on a concave end of a glenoid component. On the contrary, a second type of prothesis, defined inverse, provides a convex glenoid component that articulates on a concave humeral component. This latter prosthesis is used in critical situations of rotator cuff instability.

The glenoid component, be it of anatomic or inverse prosthesis, is fixed to an anchor element or scapular insert, which in turn is placed in contact and anchored to the scapular glenoid cavity. The humeral component is instead fixed at the top of the humerus by means of a fixing stem that is inserted in the humerus itself.

The anchor element or scapular insert usually comprises a pin for fixing the glenoid component, which is inserted into a hole formed at the glenoid cavity, and a flange having a curved shape with a convex side inserted in a seat previously formed in the glenoid cavity.

Though advantageous under various aspects and substantially satisfying the purpose, the anchor elements have a common drawback since they are not able to ensure a correct and lasting fixing of the anchor element to the scapula in case of compromised bone anatomy, with obvious serious loosening and/or detachment problems.

In particular, the known anchor elements have a standardized shape structure that is used for any patient. During the preparation step to the implant, the bone surface of the glenoid cavity is processed by removing part of the bone so as to create the seat that will then receive the anchor element. Once the anchor element has been positioned in the seat, it is stabilized by inserting stabilization bone screws.

In this way an optimal fixing of the anchor element is guaranteed in case of patients having a substantially physiologic scapular anatomy.

However, as a skilled person may well understand, the scapular anatomy of some patients may result compromised due to, for instance, resorption, deformation or poor quality of the bone tissue. In other words, the scapular bone tissue undergoes a shape and/or composition pathological alteration that varies from patient to patient. A surgeon could also face a compromised scapular anatomy in case of a revision surgery of a shoulder joint prosthesis.

In case of important alterations of the scapular anatomy, the surgeon may have serious difficulties in obtaining the seat for the application of the anchor element and in the stabilization of the latter to the bone. As a consequence, the anchor element does not adequately match the below bone surface with the consequent impairment of the implant stability.

A solution adopted to ensure the stabilization of the glenoid element under conditions of compromised anatomy is to use stabilization screws that are long enough to reach the healthy bone deep in the glenoid.

Though advantageous under various aspects and substantially responding to the purpose, this solution is not always feasible due to the inter-patient heterogeneity of the pathological scapular anatomy. In fact, the standard structure of the anchor element does not allow the screws to reach the healthy bone tissue in case of particularly compromised anatomies.

An alternative solution is described in the document US 2007/01799624 that discloses a modular anatomical shoulder joint prosthesis wherein two tubular support members extend superiorly from the glenoid support and are fixed to the coracoid and acromial process, respectively, by fasteners passing therethrough. These two support members are however strut structures that does not allow a simpler insertion of fasteners or screws.

An attempt to achieve a suitable fixation of the scapular anchor in scapular anatomies of a specific patient is provided by the U.S. Pat. No. 8,532,806. Said patent described a method of manufacturing a glenoid support that matches the contour of a fractured glenoid cavity.

Though advantageous under various aspects for threating fractured glenoid cavities, this solution cannot provide adequate fixation in case of scapular anatomies in which the morphology of the glenoid cavity and/or the quality of the below bone are particularly altered.

The purpose of the present invention is to provide a scapular anchor for fixing a glenoid component of a shoulder joint prosthesis to a patient's scapula with compromised anatomy having structural and functional features such as to overcome the above drawbacks with reference to the prior art and to allow adaptability to the compromised scapular anatomies of the different patients, even with morphology of the glenoid cavity and/or the quality of the below bone particularly altered, thus ensuring a stable and lasting fixing of the anchor element to the bone.

SUMMARY OF THE INVENTION

The solution idea underlying the present invention is to customize the scapular anchor, in particular a coracoid support of said scapular anchor, according to the pathological scapular anatomy of the single patient.

The customization can be implemented while manufacturing the anchor based on a faithful reconstruction of the patient's anatomy or possibly in the implantation step.

Based on such a solution idea, the previously identified technical problem is solved by a scapular anchor according to claim 1.

The customized portion of the implant is directly made to match the bone surface in the implantation step and does not need a reception seat. Obtaining the reception seat can be a task difficult to perform in case of severely compromised scapular anatomy due to deformation, reabsorption or poor quality of the pathological bone tissue.

By making the anchor perfectly match the bone surface, the stability of the anchor to the pathological scapular anatomy is promoted.

The customized portion can advantageously be the flange of the glenoid support, namely the distal surface of the flange having a substantially convex and wavy shape such as to shape to the bone morphology of the glenoid cavity.

Further customized portions can advantageously be represented by a coracoid support projection arranged to shape to the bone morphology of a coracoid process of the scapula and/or by at least one acromial support projection arranged to shape to the bone morphology of an acromial process of the scapula.

In case of scapular anatomies in which the morphology of the glenoid cavity and/or the quality of the below bone are particularly altered, the sole fixing of the scapular anchor to the glenoid cavity does not ensure a stable and lasting fixing. The presence of at least one coracoid support projection and/or at least one acromial support projection allows fixing the scapular anchor to other bone components of the scapula in order to obtain a proper fixing.

The coracoid support projection can have a substantially tubular shape with a proximal end integral with the glenoid support and a second distal end adapted to abut to the coracoid process of the scapula; a through-hole can advantageously extend between the proximal end and the distal end for inserting a stabilization bone screw to the coracoid process of the scapula.

Likewise, the acromial support projection can have a substantially tubular shape with a proximal end integral with the glenoid support and a second distal end adapted to abut to the acromial process of the scapula; a through-hole can advantageously extend between the proximal end and the distal end for inserting a stabilization bone screw to the acromial process of the scapula.

The distal surface of the glenoid support, the coracoid and acromial support projections can therefore be directly designed based on a faithful reconstruction of the compromised scapular anatomy of the single patient.

In particular, the at least one coracoid and/or acromial support projection can advantageously be selected from a plurality of different modules, which can have for instance a length and/or a specific orientation with respect to the glenoid support in order to adapt to the bone morphology and to allow the fixing to the coracoid and acromial process of the scapula, respectively. In this case the support projections are assembled to the glenoid support in the implantation step, thus also facilitating the implantation process and a possible revision.

Alternatively, the coracoid and/or acromial support projection can be made in one piece with said glenoid support for instance by means of EBM sintering or SLM manufacturing.

Advantageously, the distal surface of the glenoid support and/or the distal end of the coracoid support projection and/or the distal end of the acromial support projection can have an at least partially irregular or trabecular structure to promote osteogenesis and bone integration.

Furthermore, the glenoid support can comprise at least one hole for inserting stabilization bone screws to the glenoid cavity and have the pin element made in one piece with the flange.

Anyway, the above said does not exclude the chance to have a glenoid support made of a pin and a flange, which can be assembled in the implantation step of the anchor.

The above identified technical problem can also solved by a method for manufacturing the scapular anchor. Said method can advantageously comprise a preliminary step of acquiring a bone morphology of a patient's scapula, for instance by means of computerized tomography.

The features and advantages of the scapular anchor according to the present invention will become clear from the following description of a preferred embodiment given as a non-limiting example with reference to the appended drawings.

DETAILED DESCRIPTION

Figure 1:
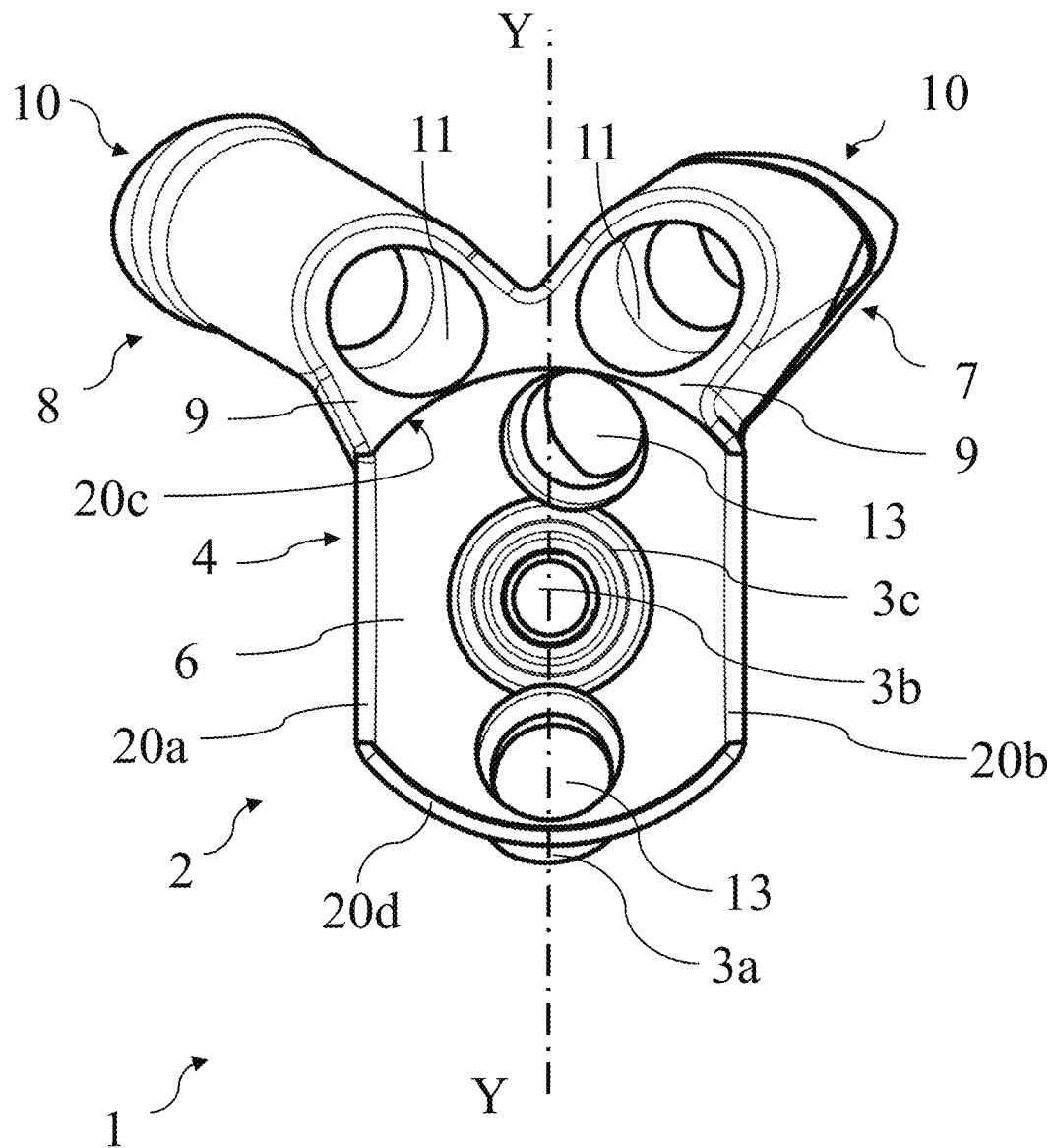
FIG. 1 shows a proximal view of a scapular anchor for an artificial prosthesis of the shoulder manufactured according to the present invention.

With reference to said figures, reference number 1 wholly and schematically indicates a preferred embodiment of an anchor element manufactured according to the present invention for stably and safely fixing a prosthesis for the shoulder joint to a scapula having compromised bone anatomy.

In the following of the description we will refer to this anchor element 1 with the easier term of "scapular anchor".

Advantageously, the anchor 1 is a customizable component to be adapted to the compromised anatomy of the single patient.

The customization of the anchor can occur in the manufacturing step of the device or it can be directly carried out by the surgeon in the implantation step of the shoulder prosthesis.

In the first case, the anchor morphology is adapted for each patient based on a faithful reconstruction of the compromised scapular anatomy implemented by the modern computerized tomography techniques. Said approach allows shaping the anchor so that in the implantation step it perfectly matches the articular bone surface which it will have to be fixed to.

On the contrary, in the second case the anchor has portions, which are standardized but at the same time modulable, allowing the surgeon to choose the anchor configuration that best suits the patient's anatomy in the implantation step.

The preferred embodiment described in the following falls within the first customization case above described and in particular the anchor 1 is designed based on the model of a compromised scapular anatomy shown in FIGS. 5-9. This does not exclude other customization ways of the anchor according to the compromised anatomy of the single patient.

The anchor 1 shown in the appended figures comprises three portions for fixing to various bone sites of the scapula 50 with compromised anatomy: a glenoid support 2, a coracoid support projection 7 and an acromial support projection 8, arranged for fixing the anchor 1 to a glenoid cavity 51, to a coracoid process 52 and to an acromial process 53 of the scapula 50, respectively.

Other embodiments can provide a glenoid support 2 with one or more coracoid support projections 7 and/or one or more acromial support projection 8.

The anchor 1 is made of a biocompatible metal material, for instance of titanium or an alloy thereof and has a macro-rough finish, for instance according to what is described in U.S. Ser. No. 12/601,510 patent.

As it can be noticed from FIGS. 1-4 showing the anchor 1 in itself, the glenoid support 2 comprises a pin element 3 that is hollow and extended along a longitudinal axis X-X with a longitudinal dimension greater than its diameter or than its radial size.

The outer surface of the pin element 3 has longitudinal grooves to promote osteogenesis and bone integration when inserted in a hole obtained by the surgeon in the glenoid cavity 51 of the scapula 50.

The pin 3 has a tapered distal end 3a, an opposite flared proximal end 3c and is passed through by a fixing hole 3b. Within the hole 3b a glenoid component 100, 200 of a shoulder prosthesis is fixed.

A flange 4 is formed near the proximal end 3c. The above flange 4 is defined by a distal surface 5 and by a proximal surface 6, which connect to each other at a proximal edge 20.

The proximal edge 20 is defined in turn by a first lateral edge 20a opposite a second lateral edge 20b, an upper edge 20c and a lower edge 20d. The terms "lower" or "upper" are used here with reference to the prosthesis implanted on an upright patient, where the upper portion will face the head. Therefore, the preferential orientation of the anchor 1 corresponds to what is illustrated in FIG. 1.

The proximal surface 6 is a homogeneous and concave surface with a mirror pattern with respect to a symmetry axis Y-Y that is orthogonal to the axis X-X. On the bottom of the proximal surface 6 the flared proximal end 3c of the pin 3 and two stabilization through-holes 13 for the insertion of corresponding stabilization bone screws 12 to the glenoid cavity 51 open. The two stabilization holes 13 end up in the distal surface 5.

In the described preferred embodiment, the stabilization holes 13 are placed one above and one below the proximal end 3c of the pin 3.

Other arrangements and number of stabilization holes 13 can be provided in other embodiments according to the anatomic shape and quality of the glenoid bone tissue of the patient.

The distal surface 5, on the contrary, has a tendentially convex shape and a non-regular wavy pattern that reproduces the pathological morphology of the glenoid cavity 51 of the scapula 50. In other words, the distal surface 5 of the glenoid support 2 is designed so as to be complementary shaped with respect to the surface of the glenoid cavity 51, which it will have to perfectly match at the time of implantation.

In particular, in the described embodiment, which is customized to match the anatomic model of FIGS. 5-9, the distal surface 5 of the glenoid support 2 wraps a first portion of the pin 3 from the closest side to the lateral edge 20a and has a tapered pattern starting from the pin 3 towards the lower edge 20c and the lateral edge 20a up to a lateral wall 20e connecting with the lateral edge 20a. At the opposite side of the pin with respect to the axis Y-Y, namely the closest one to the lateral edge 20b, the distal surface 5 wraps the proximal end 3c of the pin 3 and has a tapered pattern towards the lateral edge 20b up to a lateral wall 20f connecting with the lateral edge 20b. The lateral walls 20e, 20f are placed on planes parallel to the plane formed by the axes X-X and Y-Y.

In alternative embodiments, the distal surface 5 may possibly or optionally not be customized to adapt to the single compromised scapular anatomy and have a standard shape, for instance plane or hemispherical, coupled in the implantation step with a seat suitably obtained at the glenoid cavity 51.

Figure 2:
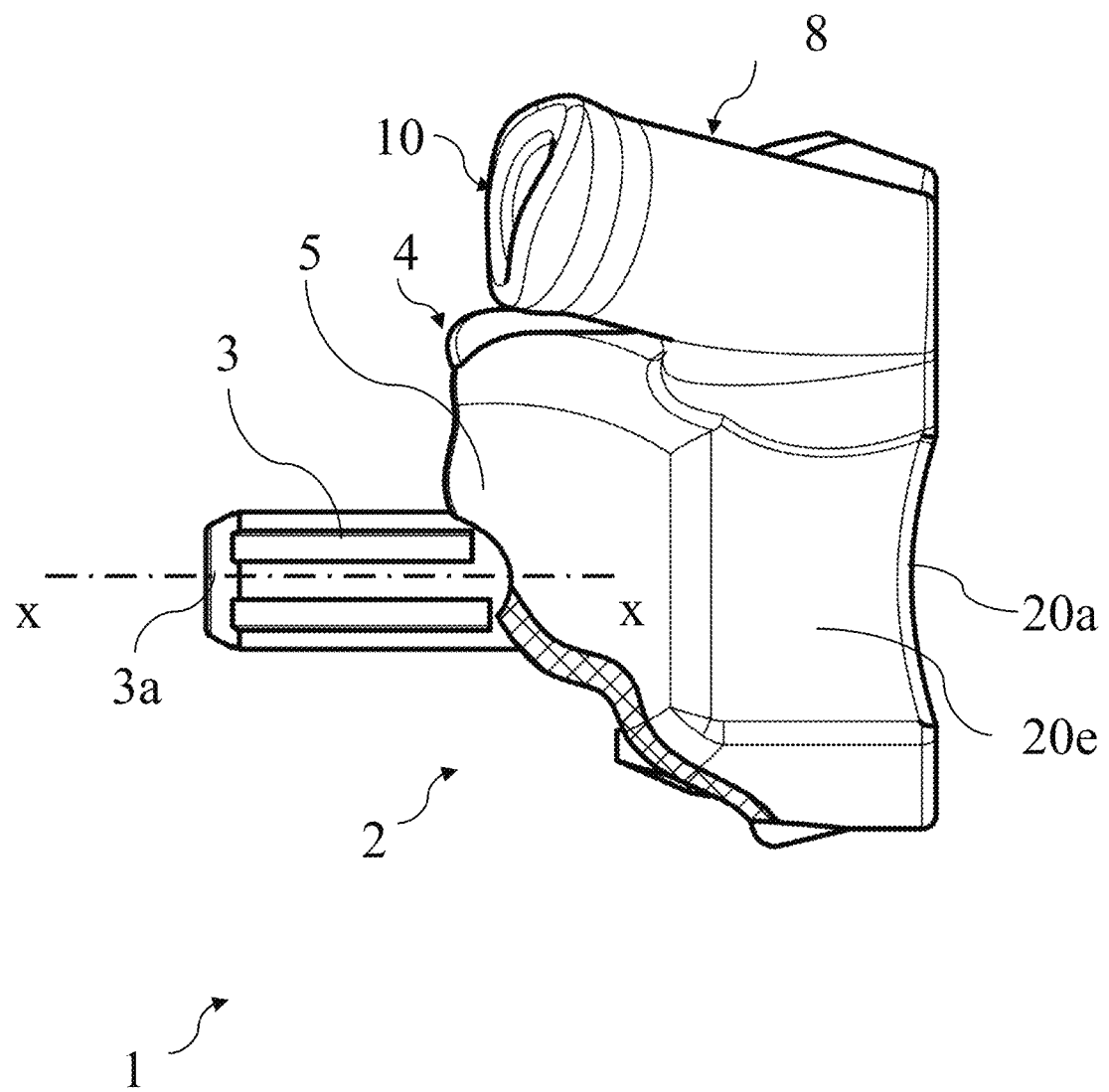
FIG. 2 shows a first side view of the scapular anchor of FIG. 1.
Figure 3:
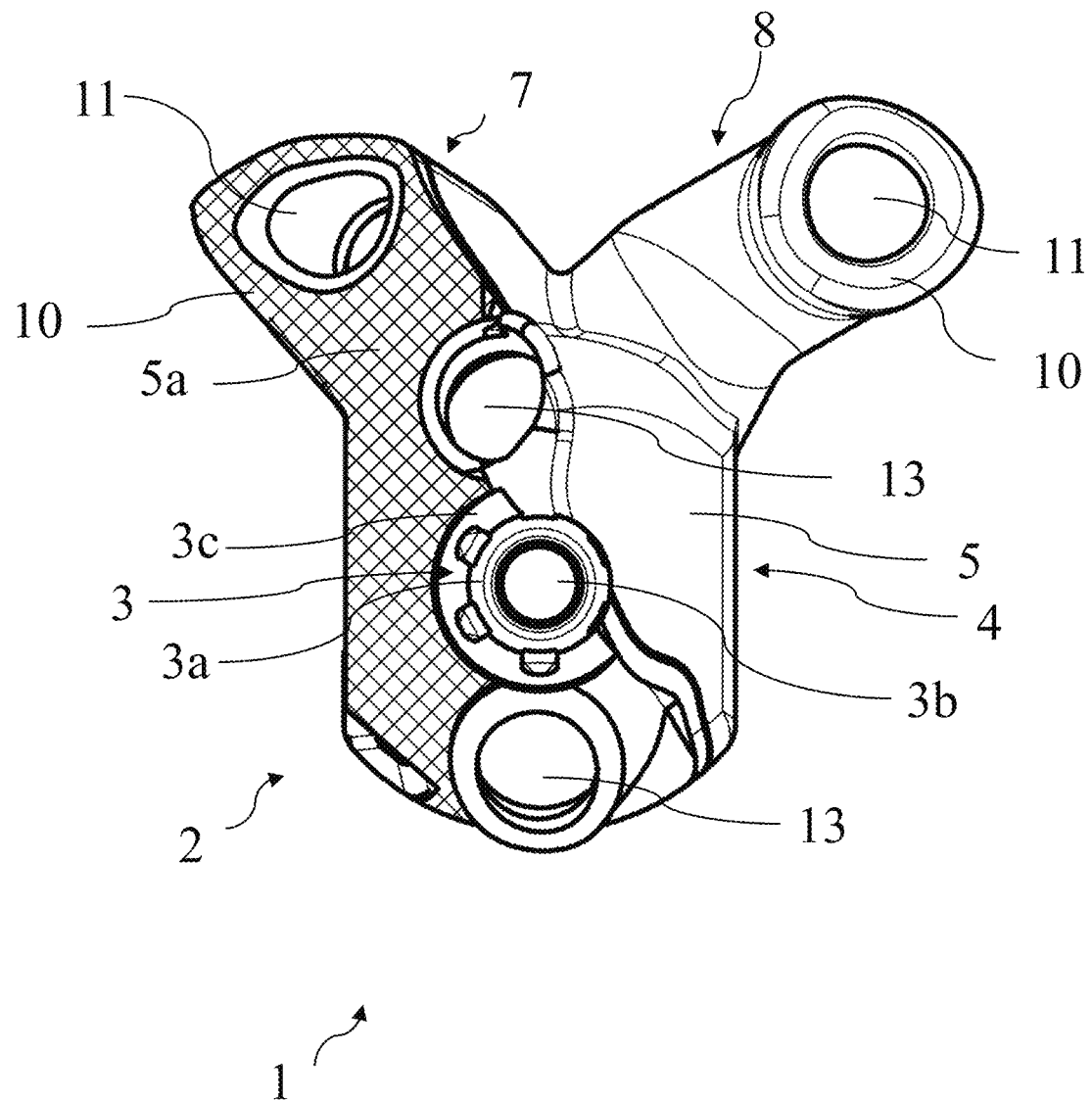
FIG. 3 shows a distal view of the scapular anchor of FIG. 1.
Figure 4:
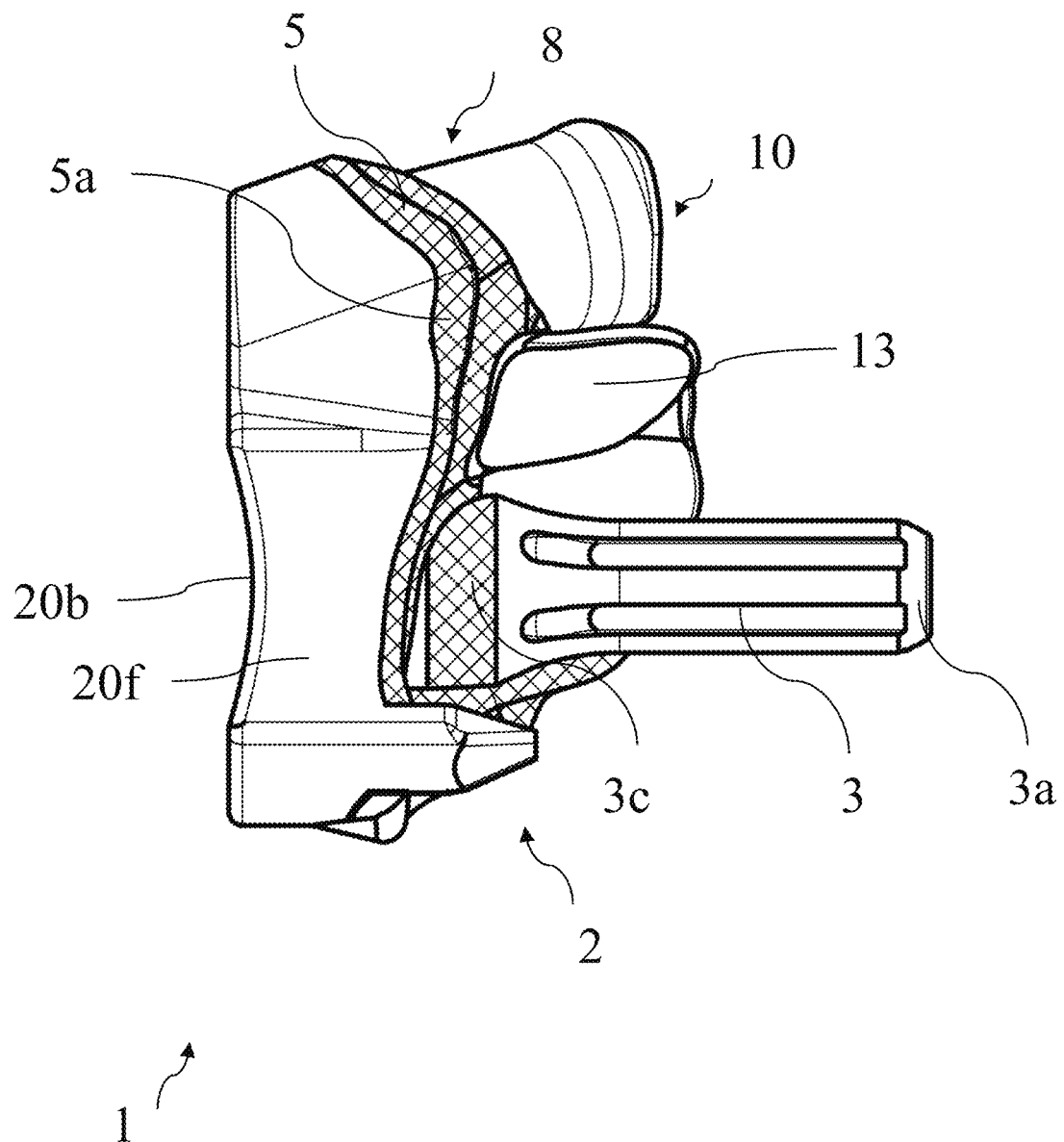
FIG. 4 shows a second side view of the scapular anchor of FIG. 1.
Figure 5:
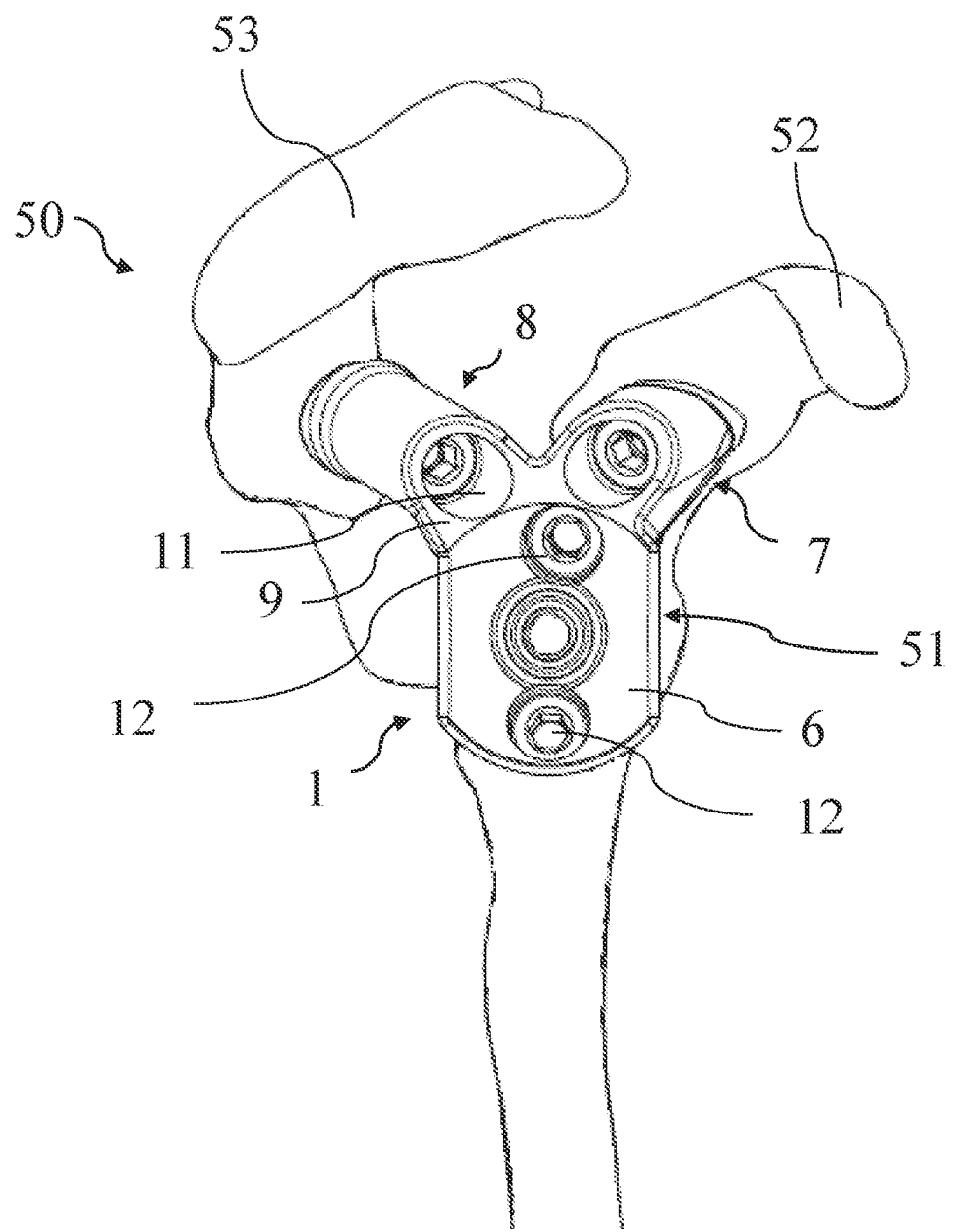
FIG. 5 shows a proximal view of the scapular anchor of FIG. 1 fixed to a scapula model with compromised anatomy.
Figure 6:
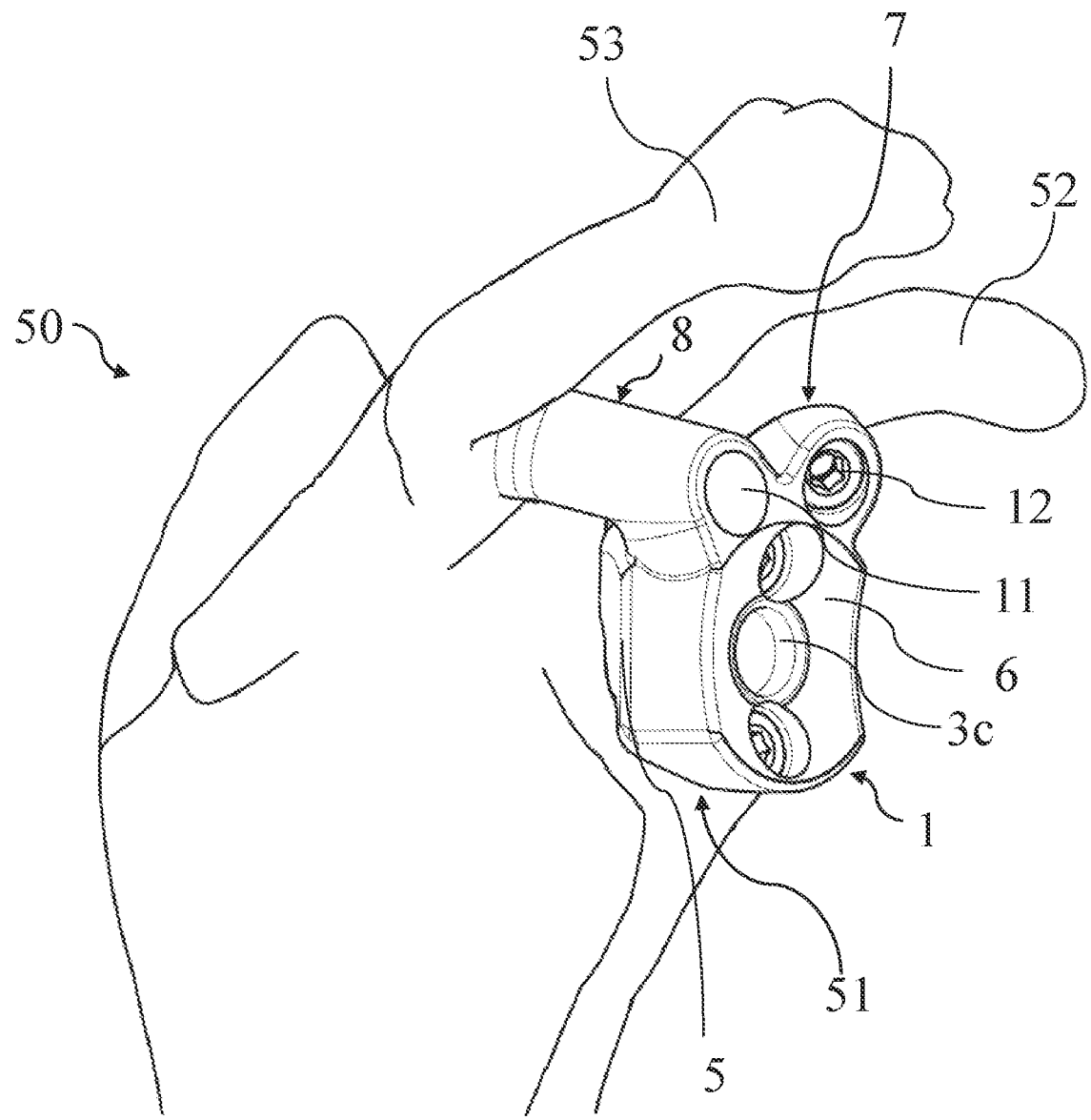
FIG. 6 shows a perspective view of the scapular anchor of FIG. 1 fixed to a scapula model with compromised anatomy.
Figure 7:
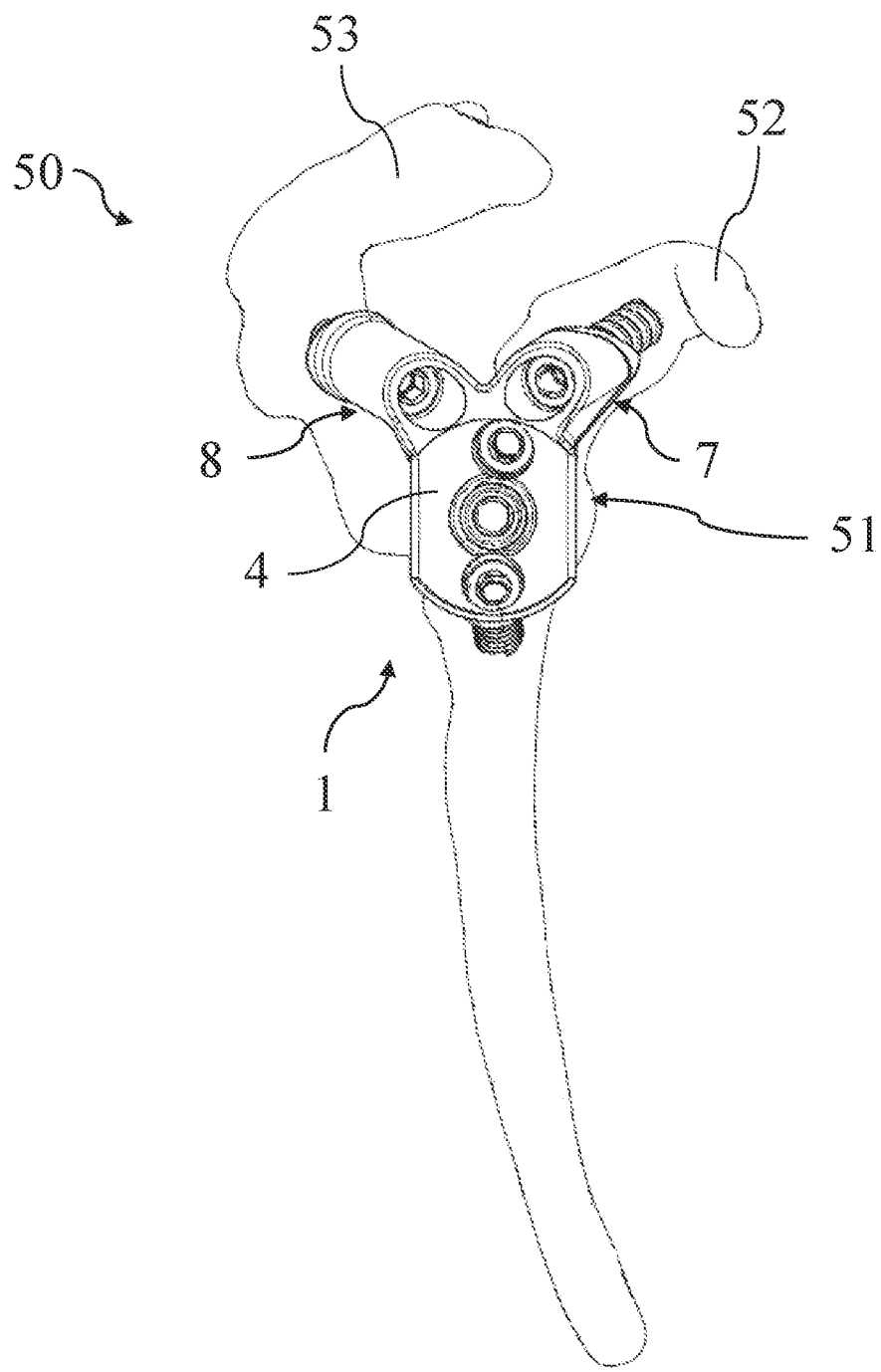
FIG. 7 shows a proximal view in transparency of the scapular anchor of FIG. 1 fixed to a scapula model with compromised anatomy.
Figure 8:
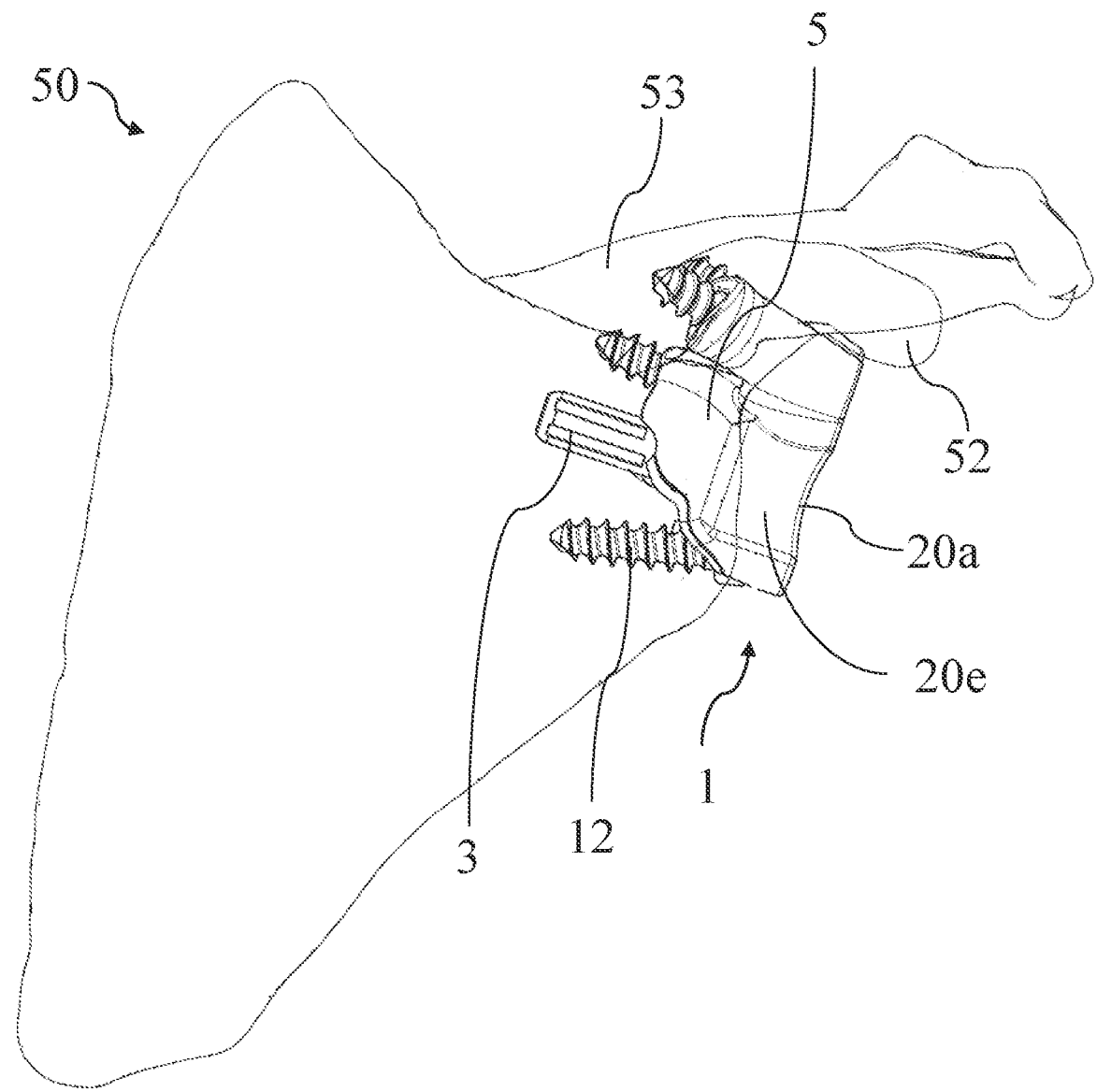
FIG. 8 shows a first side view in transparency of the scapular anchor of FIG. 1 fixed to a scapula model with compromised anatomy.
Figure 9:
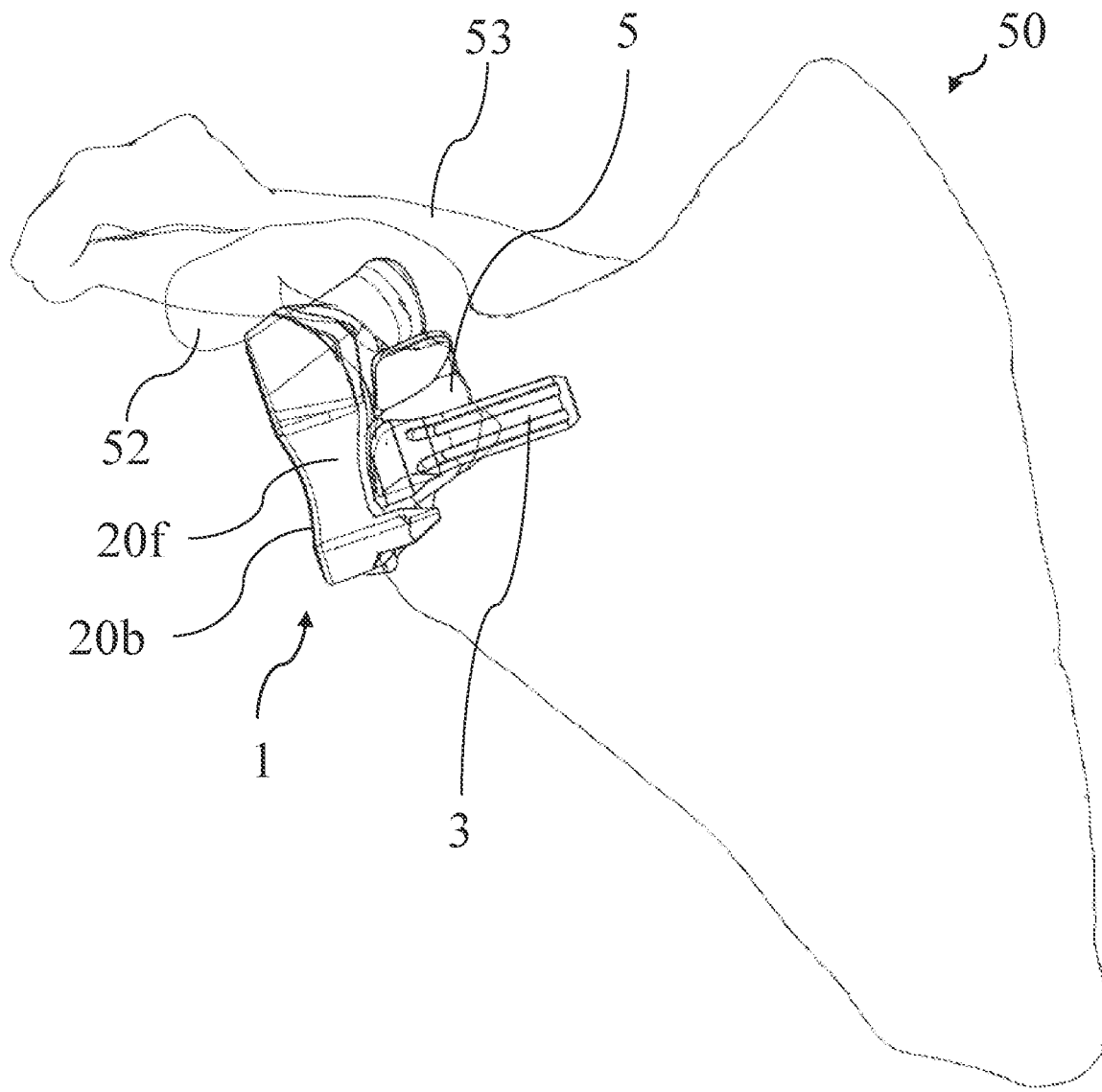
FIG. 9 shows a second side view in transparency of the scapular anchor of FIG. 1 fixed to a scapula model with compromised anatomy.

As it is clear from FIGS. 2 and 4, the pin element 3 passes through the distal surface 5 protruding away therefrom. The pin element 3 can be made in one piece with the flange 4 or constrained to the latter by interference.

At the upper edge 20c the coracoid 7 and acromial 8 support projections depart.

The support projections 7, 8 have a substantially tubular shape wherein a through-hole 11 extends from a proximal end 9 to a distal end 10. The proximal ends 9 of the support projections 7, 8 converge close to the axis Y-Y, but then the two support projections 7, 8 follow a divergent pattern away from the plane defined by the axes X-X and Y-Y and by the distal surface 5.

The through-holes 11 of the coracoid 7 and acromial 8 support projections allow the insertion of stabilization screws 12 for fixing to the coracoid 52 and acromial 53 processes, respectively.

In alternative embodiments the support projections 7, 8 may take up different shapes, not be provided with a through-hole 11 and be fixed in other ways known in the field, for instance by interference without using any fixing means.

In the described preferred embodiment, the coracoid 7 and acromial 8 support projections are made in one piece with the glenoid support 2. For instance, the projections can be made by EBM sintering or SLM manufacturing processes. Alternative embodiments can instead provide projections 7, 8 assembled with the glenoid support 2 in the implantation step of the anchor 1 so as to facilitate the surgery and possible future revisions.

Anyway, the support projections 7, 8 have a length and an orientation designed according to the compromised scapular anatomy 50 so that, when the anchor 1 is implanted, the distal end 10 abuts against the corresponding surface of the bone process 52, 53, which the projection 7, 8 is fixed to by means of the stabilization screw 12.

As it is clear from FIGS. 2 and 4, the distal end 10 of the coracoid support projection 7 and part of the distal surface 5 of the below glenoid support 2 have an irregular or trabecular structure 5a to promote osteogenesis and bone integration and was chosen to increase the contact friction of the distal end 10 and of the glenoid support 2 with respect to the surface of the coracoid process 7 and of the glenoid cavity 51 which it is respectively coupled to. This does not exclude that other surfaces or all of the surfaces in contact with the bone can be manufactured with a trabecular structure.

Therefore, each projection 7 or 8 has a shape that can be customized for any patient in the implantation step, by adjusting for instance length and/or orientation thereof, adapting it to the specific anatomy of the coracoid 52 and acromial 53 processes of the patient prior to the manufacturing step.

FIGS. 5-9 show the preferred embodiment of the scapular anchor 1 fixed to a scapula model with compromised anatomy, which it has been specifically designed for.

As it can be noticed from the above cited figures, the glenoid support 2 is implanted by making the distal surface 6, excluding the lateral walls 20e, 20f, match the glenoid cavity 51, which it perfectly coincides with. At the same time, the pin element 3 is inserted in a hole suitably formed in the glenoid cavity 51 and the stabilization screws 12 are inserted in the stabilization holes 8 and screwed to the bone below.

A further support is ensured by the two coracoid 7 and acromial 8 support projections that engage the distal end 10 against the respective coracoid 52 and acromial 53 process which they are fixed to by means of stabilization screws 12 inserted through the proximal end 9 into the through-hole 11.

Once the scapular anchor 1 has been fixed to the patient's scapula 50, as just described, the glenoid component 100, 200 of the shoulder total prosthesis is fixed thereto, said glenoid component 100, 200 will articulate with a humeral component 101, 201 previously fixed at the top of the humerus by means of a humeral stem 102, 202.

Figure 10:
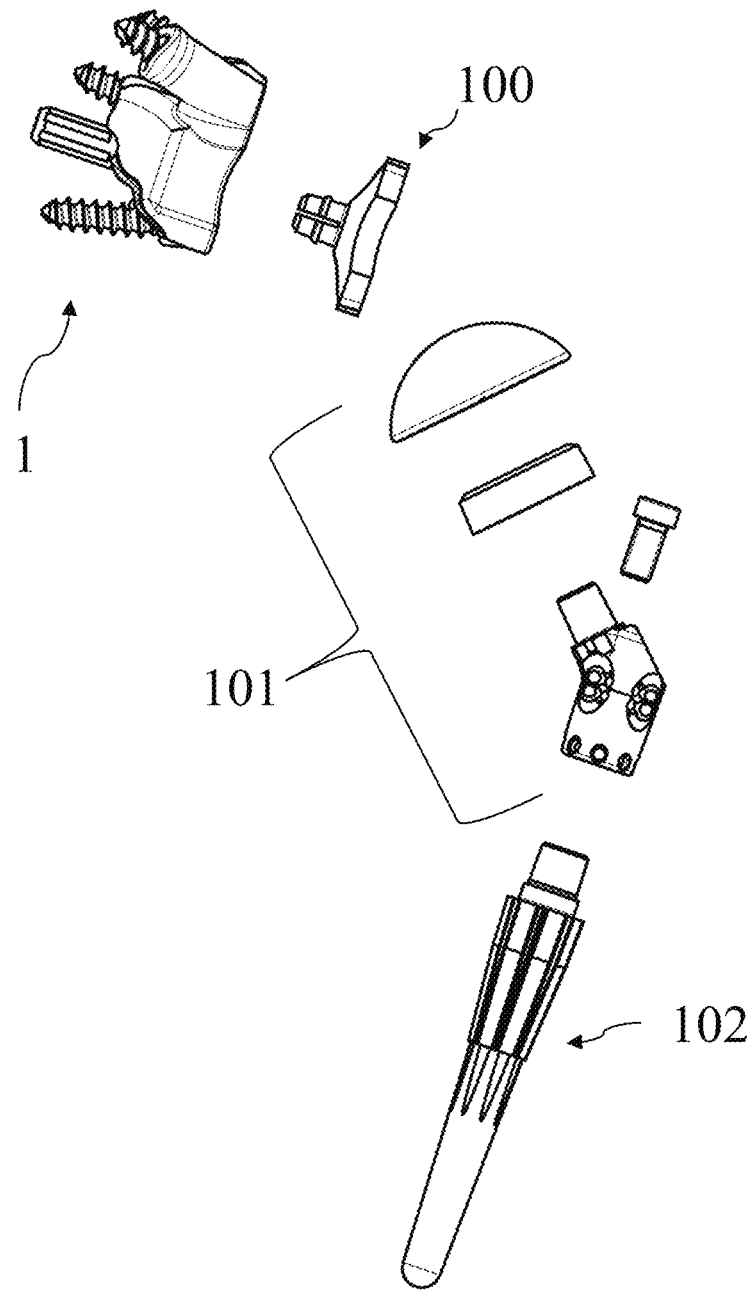
FIG. 10 is a side view showing detached parts of an anatomical total artificial shoulder prosthesis comprising a scapular anchor according to the present invention.
Figure 11:
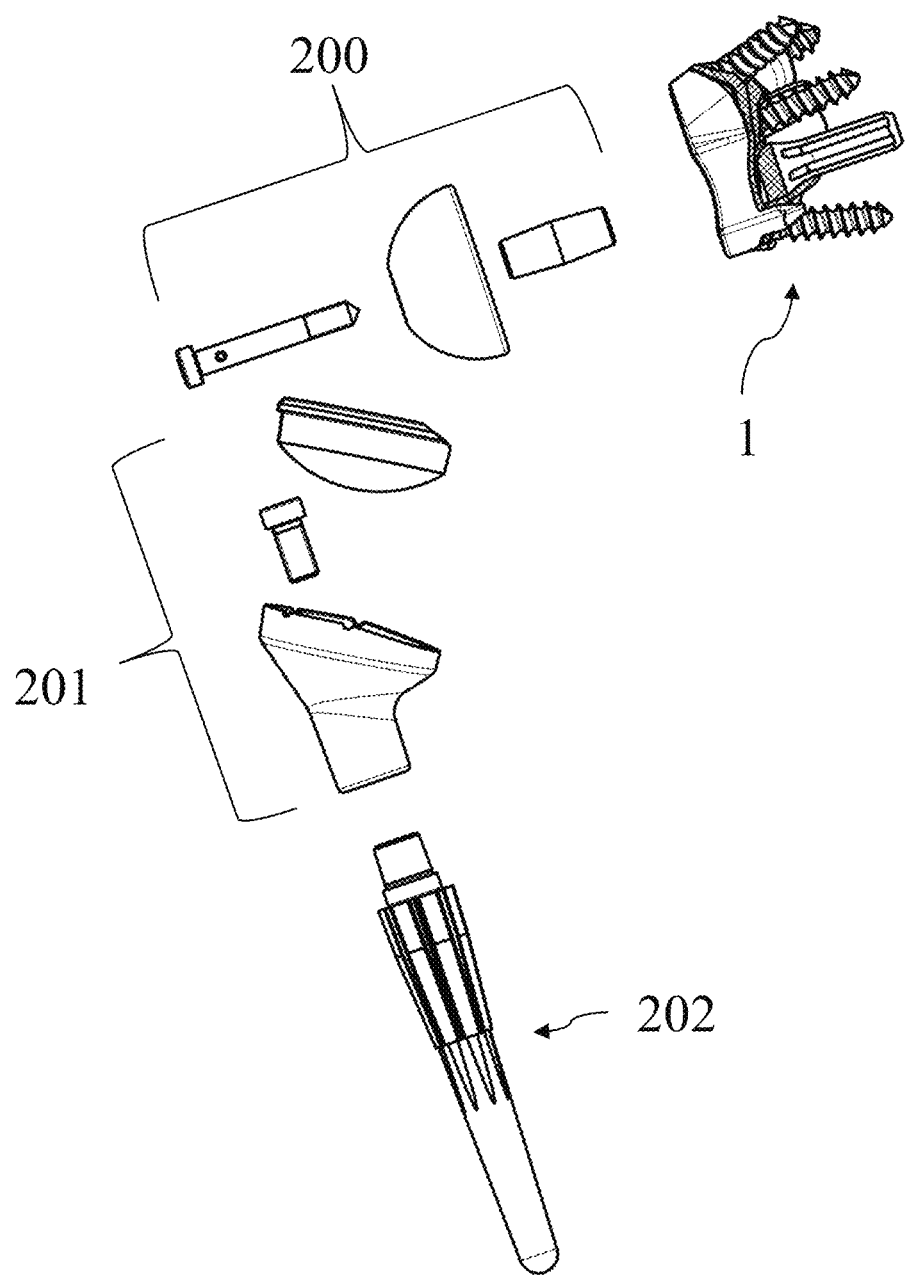
FIG. 11 is a side view showing detached parts of an inverse total artificial shoulder prosthesis comprising a scapular anchor according to the present invention.

FIGS. 10 and 11 is a side view showing detached parts of a total artificial shoulder prosthesis, anatomic and inverse respectively, comprising a scapular anchor 1 according to the present invention.

It is described a method for manufacturing a scapular anchor for fixing a glenoid component of a shoulder joint prosthesis to a patient's scapula with compromised anatomy, of the type comprising the steps of providing a glenoid support, said glenoid support being defined by a pin for fixing said glenoid component to said scapular anchor and a flange integral with said pin, said flange having a distal surface adapted to be at least partially in contact with a glenoid cavity of said scapula and a proximal surface opposite said distal surface The method for manufacturing a scapular anchor comprises a step of specifically providing at least one customized portion of said scapular anchor shaped to match the bone morphology of a scapula of a single patient with compromised anatomy and in that said at least one customized portion comprises at least one coracoid support projection arranged to abut at a coracoid process of said scapula.

The method for manufacturing a scapular anchor comprises a step of acquiring a bone morphology of a patient's scapula, for example by computerized tomography, prior to the step of shaping said custom portion of the scapular anchor.

It is further described a method for manufacturing a scapular anchor for fixing a glenoid component of a shoulder joint prosthesis to a patient's scapula with compromised anatomy; the method including the steps of: providing a glenoid support including a flange and a pin integral with the flange for fixing said glenoid component to said scapular anchor; said flange having a distal surface structured to be at least partially in contact with a glenoid cavity of said scapula and an opposite proximal surface; providing at least one customized portion of said scapular anchor specifically shaped to match the bone morphology of the scapula of a single patient with compromised anatomy; said at least one customized portion comprising at least one coracoid support projection having a substantially tubular shape integrally formed with said glenoid support and structured to abut at a coracoid process of said scapula.

According to the method for manufacturing a scapular anchor, a proximal end of said at least one coracoid support projection being formed adjacent to said glenoid support while a distal end of said at least one coracoid support projection being structured to abut to said coracoid process of said scapula; a through-hole extending between said proximal end and said distal end for receiving a stabilization bone screw into said coracoid process of said scapula.

The method for manufacturing a scapular anchor further comprises a step of acquiring a bone morphology of a patient's scapula, for example by computerized tomography, prior to the step of shaping said custom portion of the scapular anchor.

From the above description it is clear that the anchor according to the present invention achieves the intended purposes and several advantages, the main of which are hereinbelow listed.

Essentially, the solution of the present invention provides a customized scapular anchor in the design or implantation step to adapt to the particular compromised scapular anatomy of the single patient, detected for instance by computerized tomography.

Advantageously, the scapular anchor provides a glenoid support that can be complementary shaped with respect to the glenoid cavity which it perfectly matches once it has been implanted, thus promoting the implant stability.

Advantageously, the scapular anchor provides a coracoid support projection and/or an acromial support projection that offer a further support for the stabilization and fixing of the anchor to the scapula. Said projections can advantageously be customized in the design or implantation step to adapt to the particular anatomy of the coracoid and acromial processes of the patient.

Advantageously, the distal surface of the glenoid support and/or the second distal end of the coracoid and/or acromial support projection can have an irregular or trabecular structure to promote osteogenesis and bone integration.

The invention claimed is:

1. A scapular anchor for fixing a glenoid component of a shoulder joint prosthesis to a patient's scapula with compromised anatomy, comprising:
   a glenoid support defined by a pin for fixing said glenoid component to said scapular anchor and by a flange integral with said pin, said flange having a distal surface adapted to be at least partially in contact with a glenoid cavity of a scapula and a proximal surface opposite said distal surface;
   wherein said scapular anchor comprises at least one customized portion specifically shaped with respect to a bone morphology of the scapula of a single patient with compromised anatomy;
   wherein said at least one customized portion comprises at least one customized coracoid support projection arranged to abut at a coracoid process of said scapula and having a substantially tubular shape having a proximal end adjacent to said glenoid support and a distal end adapted to abut to said coracoid process of said scapula;

wherein said at least one customized coracoid support projection is made in one piece with said glenoid support;

wherein a through-hole extends between said proximal end and said distal end of said at least one customized coracoid support projection, for inserting a stabilization bone screw into said coracoid process of said scapula.

2. The scapular anchor of claim 1, wherein said at least one customized portion further comprises the distal surface of said flange, being a customized distal surface of said flange, complementary shaped with respect to the glenoid cavity of said scapula.

3. The scapular anchor of claim 1, further comprising at least one acromial support projection adapted to be fixed to an acromial process of said scapula.

4. The scapular anchor of claim 3, wherein said at least one customized portion further comprises at least one customized acromial support projection arranged to abut at an acromion process of said scapula.

5. The scapular anchor of claim 4, wherein said at least one customized acromial support projection has a substantially tubular shape having a proximal end adjacent to said glenoid support and a distal end adapted to abut to said acromion process of said scapula.

6. The scapular anchor of claim 5, wherein a through-hole extends between said proximal end and said distal end of said customized acromial support projection, for inserting a stabilization bone screw into said acromion process of said scapula.

7. The scapular anchor of claim 4, wherein said at least one customized acromial support projection is made in one piece with said glenoid support.

8. The scapular anchor according to claim 4, wherein said at least one customized coracoid support projection and/or said at least one customized acromial support projection are structurally distinct from the glenoid support, are selected from a plurality of projections with different dimensional and/or morphological features and are assembled to the glenoid support.

9. The scapular anchor according to claim 4, wherein said distal end of said customized acromial support projection have a partially irregular or trabecular structure to promote osteogenesis and bone integration.

10. The scapular anchor according to claim 1, wherein said glenoid support comprises at least one hole for inserting stabilization bone screws to stabilize said glenoid support to said glenoid cavity.

11. A scapular anchor for fixing a glenoid component of a shoulder joint prosthesis to a patient's scapula with compromised anatomy, comprising:

a glenoid support including a flange and a pin integral with the flange for fixing said glenoid component to said scapular anchor;

said flange having a distal surface structured to be at least partially in contact with a glenoid cavity of said scapula and an opposite proximal surface;

said scapular anchor comprising at least one customized portion specifically shaped to match a bone morphology of a scapula of a single patient with compromised anatomy;

said at least one customized portion comprises at least one coracoid support projection having a substantially tubular shape integrally formed with said glenoid support and structured to abut at a coracoid process of said scapula;

a proximal end of said at least one coracoid support projection being adjacent to said glenoid support;

a distal end of said at least one coracoid support projection being structured to abut to said coracoid process of said scapula;

a through-hole extending between said proximal end and said distal end for inserting a stabilization bone screw into said coracoid process of said scapula.

12. The scapular anchor according to claim 11, wherein said at least one customized portion further comprises at least one customized acromial support projection arranged to abut at an acromion process of said scapula.

13. The scapular anchor according to claim 12, wherein said at least one customized acromial support projection has a substantially tubular shape having a proximal end adjacent to said glenoid support and a distal end adapted to abut to said acromion process of said scapula.

14. The scapular anchor according to claim 13, wherein a through-hole extends between said proximal end and said distal end for inserting a stabilization bone screw into said acromion process of said scapula.

15. The scapular anchor according to claim 12, wherein said customized acromial support projection is made in one piece with said glenoid support.

16. The scapular anchor according to claim 11, wherein said at least one customized portion further comprises at least the distal surface of said flange, said distal surface being complementary shaped with respect to the glenoid cavity of said scapula.

17. The scapular anchor according to claim 12, wherein said customized acromial support projection is structurally distinct from the glenoid support, is selected from a plurality of projections with different dimensional and/or morphological features and are assembled to the glenoid support.

18. The scapular anchor according to claim 12, wherein said distal end of said customized acromial support projection has a partially irregular or trabecular structure to promote osteogenesis and bone integration.

19. The scapular anchor according to claim 11, wherein said glenoid support comprises at least one hole for inserting stabilization bone screws to stabilize said glenoid support to said glenoid cavity.

20. The scapular anchor according to claim 1, wherein said distal surface of said glenoid support has a partially irregular or trabecular structure to promote osteogenesis and bone integration.

21. The scapular anchor according to claim 1, wherein said distal end of said at least one customized coracoid support projection has a partially irregular or trabecular structure to promote osteogenesis and bone integration.

* * * * *